US012566164B2

(12) United States Patent
Fernandez Huerta et al.

(10) Patent No.: US 12,566,164 B2
(45) Date of Patent: Mar. 3, 2026

(54) EQUIPMENT FOR MEASURING GASES AND ENVIRONMENTAL PARAMETERS

(71) Applicant: KUNAK TECHNOLOGIES, S.L., Orcoyen (ES)

(72) Inventors: Francisco Javier Fernandez Huerta, Orcoyen (ES); Francisco Javier Alonso Caballero, Orcoyen (ES)

(73) Assignee: KUNAK TECHNOLOGIES, S.L., Orcoyen (ES)

( * ) Notice: Subject to any disclaimer, the term of this patent is extended or adjusted under 35 U.S.C. 154(b) by 256 days.

(21) Appl. No.: 18/000,723

(22) PCT Filed: May 19, 2021

(86) PCT No.: PCT/ES2021/070359
§ 371 (c)(1),
(2) Date: Dec. 5, 2022

(87) PCT Pub. No.: WO2021/250298
PCT Pub. Date: Dec. 16, 2021

(65) Prior Publication Data
US 2023/0213492 A1    Jul. 6, 2023

(30) Foreign Application Priority Data
Jun. 11, 2020    (ES) ................................ ES202030571

(51) Int. Cl.
G01N 33/00          (2006.01)
(52) U.S. Cl.
CPC ................................ G01N 33/0031 (2013.01)
(58) Field of Classification Search
CPC .......... G01N 33/0031; G01N 33/0004; G01N 33/0009; G01N 15/1012; G01N 21/274;
(Continued)

(56) References Cited

U.S. PATENT DOCUMENTS

2015/0354983 A1* 12/2015 Lee ........................... G01J 5/04
73/431
2018/0041606 A1    2/2018 Luo et al.
(Continued)

FOREIGN PATENT DOCUMENTS

CN        210604585 U      5/2020
DE   202017106435 U1 * 12/2017   ........... H05K 5/0013
(Continued)

OTHER PUBLICATIONS

International Search Report for Corresponding International Application No. PCT/ES2021/070359, 3 pages, Aug. 23, 2021.

*Primary Examiner* — John E Breene
*Assistant Examiner* — Truong D Phan
(74) *Attorney, Agent, or Firm* — LUCAS & MERCANTI, LLP

(57) ABSTRACT

A measurement equipment for measuring gases and environmental parameters, made up of sensors (4) for measuring the parameters that influence air quality, odors, leak detection, fugitive emissions, pollutants, the presence of certain gases in the atmosphere, etc., having a housing (1) configured to incorporate removable cartridges (3) in which sensors (4) are housed, associated in an assembly unit with respective specific electronic boards (5) which are connected to a central electronic board (6) arranged in the housing (1) that recognizes the sensors (4). A cartridge (3) configured to be coupled to the measurement equipment for measuring gases and environmental parameters.

6 Claims, 7 Drawing Sheets

(58) Field of Classification Search
CPC .............. G01N 21/93; G01N 27/3274; G01N
27/4163; G01N 27/4175; G01N 27/9086;
G01N 2030/626; G01N 30/8665; G01N
33/0006; G01N 1/22; G01N 33/0008;
G01N 33/007; G01N 33/0075; G01N
33/0073; G01N 35/00594; G01N
2035/00683; G01N 35/00693; G01N
2201/127; G01N 2201/12715; G01N
2201/12746; G01N 2201/1273; G01D
18/00; G01D 18/004; G01D 18/006;
G01D 18/008; G01D 18/002; G01D
2218/00
USPC ......................................................... 73/23.2
See application file for complete search history.

(56) References Cited

U.S. PATENT DOCUMENTS

| | | | |
|---|---|---|---|
| 2018/0120279 A1 | 5/2018 | Yi et al. | |
| 2018/0243527 A1 | 8/2018 | Zapol et al. | |
| 2021/0018210 A1 * | 1/2021 | Nasis ........................ | F24F 11/65 |

FOREIGN PATENT DOCUMENTS

| | | | | | |
|---|---|---|---|---|---|
| EP | 3518202 A1 | 7/2019 | | | |
| EP | 3518202 B1 * | 4/2021 | .............. | F24F 11/30 | |
| JP | WO2004111627 A1 * | 10/2006 | ......... | G01N 33/0009 | |
| KR | 102070228 B1 | 1/2020 | | | |
| WO | 2015160830 A1 | 10/2015 | | | |
| WO | 2016196862 A1 | 12/2016 | | | |

* cited by examiner

EQUIPMENT FOR MEASURING GASES AND ENVIRONMENTAL PARAMETERS

CROSS REFERENCE TO RELATED APPLICATION

This Application is a 371 of PCT/ES2021/070359, filed on May 19, 2021 which claims the benefit of Spanish Patent Application No. P202030571, filed on Jun. 11, 2020, each of which are incorporated herein by reference.

TECHNICAL FIELD

The present invention relates to measurement equipment for quantifying environmental variables that have an influence on air quality, odors or fugitive emissions, proposing equipment for measuring gases and suspended particles in combination with other environmental variables, in which specific sensors for these variables are used, with an embodiment that improves the manufacturing characteristics (production, characterization, testing and validation), operation, assembly and maintenance of this type of apparatus.

STATE OF THE ART

The measurement of emission gases is essential in many aspects and applications, with there being equipment which allows measuring gases and suspended particles by means of sensors in order to quantify their impact on the alteration of environmental conditions.

Conventional equipment of this type includes a series of specific sensors for measuring the different variables to be quantified, with said sensors being linked to electronics that collect data provided by the sensors in order to establish an assessment of the state of the environment based on the measurements taken.

To that end, sensors of different types and manufacturing origins can be used in the measurement equipment with several variants in terms of electrical connections and form factors, which has an impact on the mechanical design of the measurement equipment that must be adapted for the different sensors and on the need for specific signal conditioners for each sensor. The individual characterization of the sensor that is introduced in the measurement equipment is required, which means that the sensor can only work optimally with that equipment and not with another equipment, and when one sensor is replaced by another, it is necessary to configure the equipment and recalibrate it again by having to move the equipment to a laboratory or by means of expensive mobile laboratories in many cases.

It should also be taken into account that the diversity of sensors that can be incorporated into measurement equipment generally have common characteristics that may be relevant in the design of application equipment, for example:

a) Many of the types of sensors used generate nanoampere currents which cause the results of the measurements being performed to be affected by any type of electromagnetic noise. It means that, being such small currents, it is necessary to amplify these signals to the extent possible in order to quantify them, and therefore it is necessary to protect them from any external electromagnetic or environmental interference that generates false signals.

b) The response of each sensor to the various environmental conditions that it may face is unique for each sensor, so it is necessary to be able to unequivocally characterize and calibrate each of the sensors in order to achieve maximum precision.

c) The sensors can be very sensitive to temperature, humidity, atmospheric pressure, high wind speeds that degrade their performance and the presence of certain substances in the environment if it is not possible to control or correct their effects.

d) The type of material surrounding the sensors can affect the measurements performed by the sensors, since some materials can react with the gases to be measured, consequently altering the results of the measurements, so it is of great importance for the air to be measured to reach the surface of the sensor as fast as possible without interacting with other materials.

e) The mechanical design carried out can have an impact on the response time of the sensor if the air takes time to diffuse over the sensing surface and reacts with the materials surrounding same, amplifying the measurement error as mentioned in the preceding point.

f) Sensors have a limited service life, so it is necessary to replace them relatively often and to know when their reliability is reduced to a level that is not acceptable.

g) Sensor calibration must be performed by skilled technicians, which increases the costs of equipment assembly and maintenance.

h) Since sensors of this types are usually affected by the environmental conditions of the measurement, either the air is conditioned to stable conditions that are always the same or the variables which may affect the measurements are measured simultaneously to mitigate their effects.

Faced with the drawbacks entailed by that these particularities, various embodiments of measurement equipment for measuring environmental gases have been developed, but conditions of being difficult to assemble and maintain prevail in all of them as a result of shape and connection characteristics of the sensors they incorporate. In the designs of measurement equipment for measuring gases and known environmental parameters, the equipment is calibrated with already installed sensors. The arrangement of this equipment with fixed locations for each sensor means that the entire range of sensors cannot be combined with one another, because it would result in equipment the dimensions of which would be very large, so the combinations of sensors installed in the equipment is limited in this type of equipment. Once the sensors are installed, they are calibrated in the equipment, saving the calibration parameters in the equipment, so it is not possible for a sensor to be transferred to another equipment and to operate with said equipment.

Object of the Invention

According to the present invention, equipment intended for measuring the variables that influence air quality, odors or fugitive emissions is proposed, with an embodiment that provides constructive, productive and functional features capable of overcoming the limitations of conventional equipment used for said function, improving the manufacturing, production, characterization, testing and validation operations, as well as the assembly and maintenance of this type of apparatus.

The equipment object of the invention comprises a housing provided with holes to incorporate a series of cartridges, in each of which a gas measurement sensor associated with a specific electronic board can be housed, such that each sensor with its specific electronic board form an assembly unit which is inserted into the corresponding cartridge, with the functional assembly of the equipment further including a central electronic board to which the specific electronic boards of the sensors are electrically connected when the cartridges housed therein are arranged in the assembly holes in the housing.

To that end, the specific electronic board of the sensor is inserted with an electrical connector, preferably in the form of connection pins, into a connector of the cartridge, such that when the cartridge is fitted into the housing, the specific electronic board of the sensor is connected to a central electronic board of the measurement equipment. Said central electronic board has a series of standard connection ports to which the different sensors that are incorporated in the equipment by means of the cartridges are connected, the information from the sensors being recognized regardless of the position in which each cartridge is located in the housing.

Measurement equipment in which any type of gas or environmental parameter sensor can be connected regardless of its connection position to the equipment is thereby obtained, with each sensor being in an assembly unit formed by a housing cartridge, wherein the sensor is incorporated together with its specific electronic board. Said specific electronic board of each sensor incorporates the characterization, calibration and specific validation for that sensor in a memory, and allows calculating the magnitude of measurement and correction for that specific sensor for its recognition by the central electronic board with a unique algorithm for that sensor. An automatic assembly is thereby facilitated, since the cartridges housing the sensors can be operated in a very simple and removable manner, with the connection of the specific electronic board of the sensor with respect to the central electronic board, which detects which sensor it is in each case, adapting it to the function it has to perform, being effortlessly established during the placement thereof. This thereby facilitates the procedure for characterizing, calibrating and validating these sensor calibrations, being an automatic system that does not require a skilled operator to install or replace sensors, also ensuring the reliability of the measurement and the quality procedures associated with the calibration and validity of the cartridge with its specific sensor.

Said ease of assembly of the sensors also has a positive impact on the ease and economy of equipment maintenance because, when the sensors have to be replaced, given their limited operating life, it is only necessary to remove the cartridge with the unitary assembly of the sensor with its specific electronic board and to incorporate another new cartridge with a sensor having the same characteristics in its place, which does not require a skilled technician since the sensor does not have to be calibrated during assembly.

Another advantage is that a cartridge with a specific sensor can be taken out and replaced by another cartridge with a different sensor and electronic board, such that a user can carry out a measurement campaign with the equipment with a range of cartridges that measure certain parameters and then carry out another campaign with another type of cartridges. The combination of cartridges can therefore be adjusted according to needs by simply replacing one cartridge with another in the measurement equipment.

The housing cartridges of the unitary assemblies formed by the sensors associated with their corresponding specific electronic boards are also provided therein with structures, preferably stepped structures and projections, at different heights, for supporting the unitary assemblies of sensors with their specific electronic boards on said structures, which allows sensors of any size, shape and configuration to be incorporated in an assembly arrangement in which the end where the sensor has its sensing surface is flush with a level at which it is in direct contact with the air so as to reduce its response time and prevent it from coming into contact with other materials before reaching the sensor. It is also achieved that said sensing surface remains at the same level as the sensing surfaces of all the sensors incorporated in the equipment, and the same surface at which the environmental conditions of temperature, humidity, pressure are measured in different ways since this is a necessary condition for the measurements performed by the different sensors of the equipment to be as accurate as possible. It allows optimal measurement corrections to be made and any transient instability that may invalidate the measurements to be detected, since the air inside the cartridge can react with the sensor itself and modify the measurement, in addition to the fact that the response time of the sensor can be longer.

The housing cartridges for the sensors associated with their corresponding specific electronic boards are closed with a lid that secures and adjusts the position of the sensor with its specific electronic board inside the cartridge, this lid having an opening with which the sensing surface of the sensor coincides in each case, so that said sensing surface is in direct contact with the air in order to be able to detect the environmental parameters to be measured without the air interacting with any material before coming into contact with the sensing surface of the sensor as mentioned above.

This lid also ensures that the inside of the cartridge is leak-tight, preventing condensation, water or gases from being able to affect the sensor and the specific electronic board of the sensor, or from seeping into the equipment in the connection between the housing and the cartridge.

Given that the measurements performed by the sensors can be affected by variable factors, such as temperature, humidity and atmospheric pressure, among others, it is envisaged to connect to the central electronic board probes which measure these variable factors at the same level as the sensing surfaces of the sensors incorporated in the equipment, such that based on the measurements of said probes, the central electronic board makes the necessary corrections so that the values of the sensor measurements conform to reality.

Moreover, it is envisaged to incorporate a grid above the arrangement of the sensors in the equipment and covering same, which prevents sunlight and indirect radiation from striking the sensors and from being able to distort the results of their measurements, with said grid in turn preventing any quick variation in air speed caused by strong wind currents from being able to have a sudden impact on the surface of the sensors, distorting their measurements, given that said grid diffuses the air inside the space where the sensors are located at maximum controlled speeds.

In order to safeguard against the detrimental impact of sunlight and the subsequent overheating that would degrade the measurement, it is also envisaged to incorporate a protective cover over the entire assembly of the equipment, said cover having openings for the circulation of air passing through the inside, such that it comes into contact with the sensing surfaces of the sensors in charge of measuring the parameters of the environmental conditions.

Based on the foregoing, the equipment object of the invention has features that make it particularly advantageous for measuring gases and environmental parameters, acquiring its own identity and a preferred character with respect to the conventional equipment used up until now for said function.

DETAILED DESCRIPTION OF THE INVENTION

Figure 1:
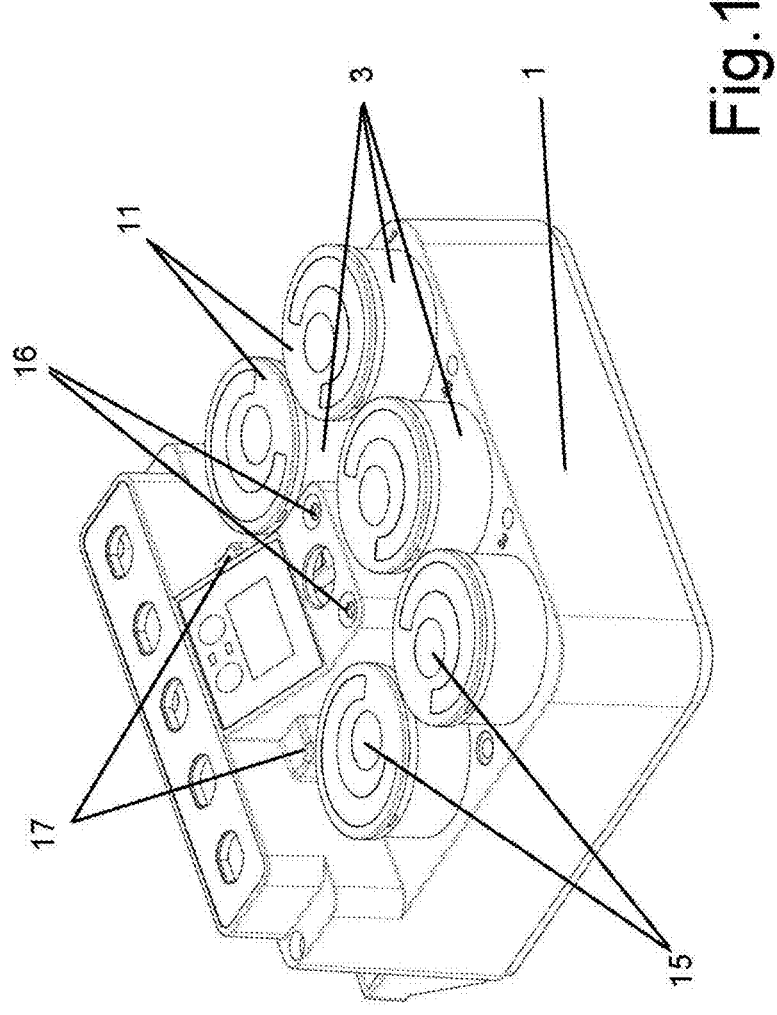
FIG. 1 shows a perspective view of an embodiment of equipment for measuring air quality, according to the invention.
Figure 2:
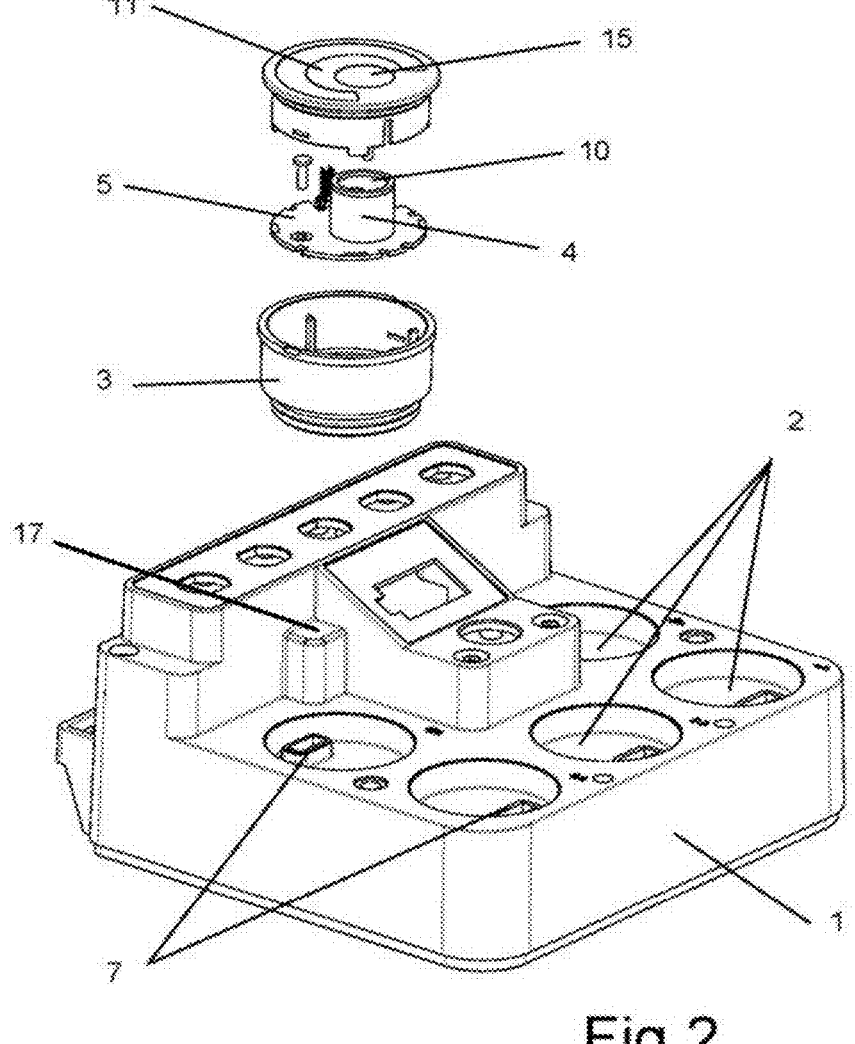
FIG. 2 is a perspective view of the body of the measurement equipment, with a housing cartridge for a sensor in an exploded arrangement according to the assembly position.
Figure 3:
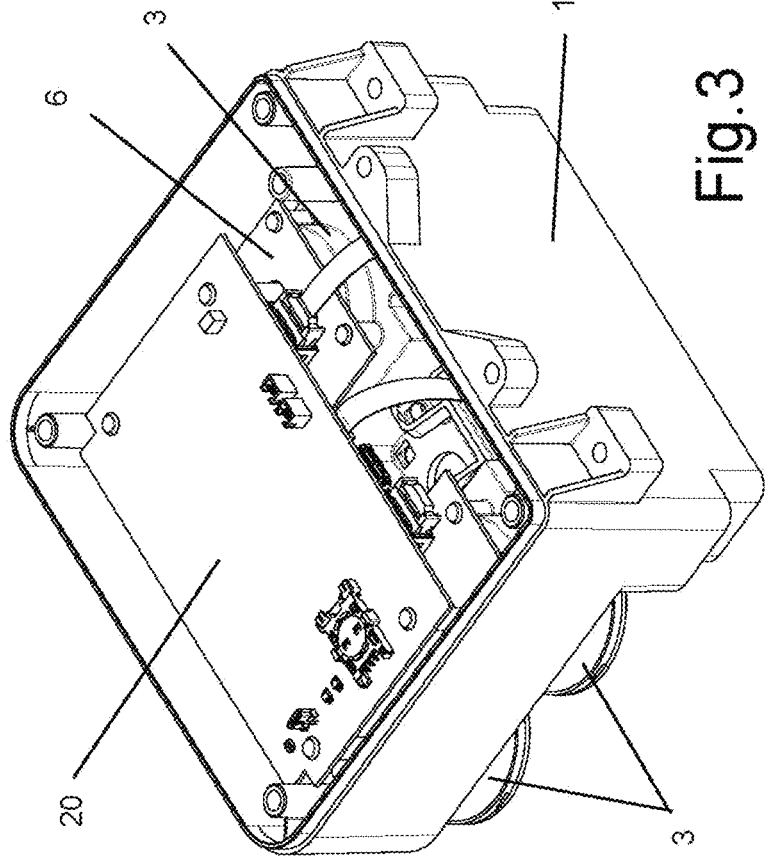
FIG. 3 is a perspective view of the measurement equipment seen from the bottom.
Figure 4:
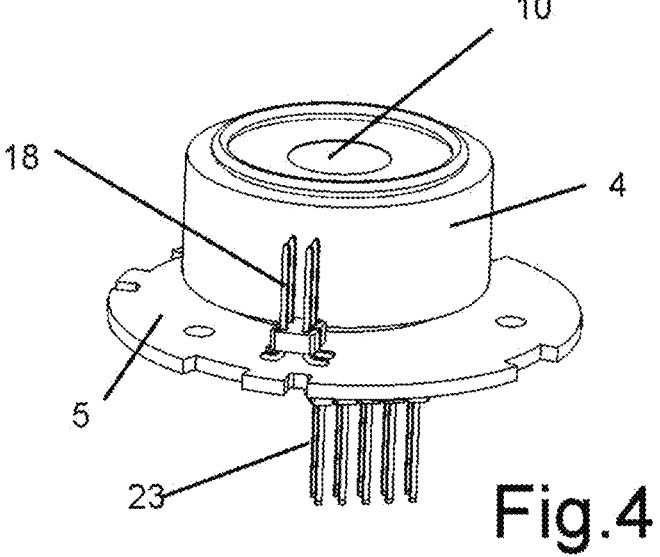
FIG. 4 shows a perspective view of the unitary assembly of a sensor associated with its specific electronic board, for incorporation in the measurement equipment according to the invention.

The object of the invention relates to equipment for measuring gases and parameters that influence, for example, air quality, odors, leak detection, fugitive emissions, pollutants, the presence of certain gases in the atmosphere, etc., comprising a housing (1) provided with holes (2) intended for fitting therein housing cartridges (3) for sensors (4) in charge of measuring gases and environmental parameters.

The sensors (4) that are arranged in the cartridges (3) are each associated with a specific electronic board (5), with the assembly of each sensor (4) with its specific electronic board (5) forming an assembly unit that is assembled in the cartridge (3) for incorporation in the measurement equipment. In this way, the sensor (4) is tested, characterized and calibrated, being validated and housed in the cartridge (3) from the factory for incorporation in the measurement equipment. The cartridge (3) with the specific electronic board (5) associated with the sensor (4) has a memory and the specific parameters for a correction algorithm of that sensor (4), such that it is only necessary to incorporate the cartridge (3) in the corresponding hole (2) of the housing (1), passing all the information from the cartridge (3) to the measurement equipment that is read by a central electronic board (6) to adjust its algorithm so as to be able to calculate the measurement magnitude.

This configuration makes it possible to do without a skilled technician, since in said assembly operation the user who receives the cartridge (3) with the sensor (4) already tested, characterized and calibrated at the factory only has to incorporate said cartridge (3) in the hole (2) of the measurement equipment being considered. This configuration also allows combining several sensors and assembling them in the different holes (2) of the measurement equipment, regardless of the type of sensor (4) incorporated in the cartridge (3).

To establish the connection between the cartridge (3) and the measurement equipment, the central electronic board (6) is provided with multiple standard connection ports, with respect to which the cartridges (3) containing the unitary assemblies formed by the different sensors (4) with their specific electronic boards (5) can be electrically connected through a connector (7) that each hole (2) of the housing (1) has at the bottom. In this way, connection pins (23) of the specific electronic board (5) are connected to a connector (8) that the cartridges (3) have therein, which in turn connects to the connector (7) of the assembly hole (2) in the housing (1).

Once the connection is established, the central electronic board (6) recognizes the cartridge (3), with the type of sensor (4) which is connected in any of the holes (2) or connection ports thereof, by reading the memory thereof included in the specific electronic board (5) of the sensor (4), being adapted particularly by means of the algorithm specific to said sensor (4) for the function that it has to perform in relation to the measurement of the environmental parameters measured by the connected cartridge (3).

These features ensure the highest quality and precision of the measurement, simplify and reduce the cost of production, testing, characterization, calibration, validation, assembly and maintenance of the measurement equipment, since the incorporation of the sensors (4) only requires placing the cartridges (3) in the assembly holes (2) in the housing (1), whereby each unit of the sensor (4) with its specific electronic board (5) is connected with the central electronic board, which automatically identifies the sensors (4) that are connected, particularly adapting the sensors to carry out their function in the measurement equipment, without requiring the intervention of a skilled expert, given that the sensors (4) do not have to be configured in said assembly.

Moreover, said condition of unity between each sensor (4) with its specific electronic board (5) and the specific parameters for its associated algorithm also has a positive impact on the replacement of the sensors (4) when they cease to be operational due to their limited service life given that, in order to replace a sensor (4), it is only necessary to remove the cartridge (3) comprising the sensor (4) along with its specific electronic board (5) from the corresponding housing hole (2) and introducing a new cartridge (3) with the new sensor (4) in its place, with the new sensor (4) automatically being ready for operation. The exchanged cartridge (3) will be discarded or can be reused in the manufacture of a cartridge (3) with a new sensor (4) configured during its manufacture.

Figure 5:
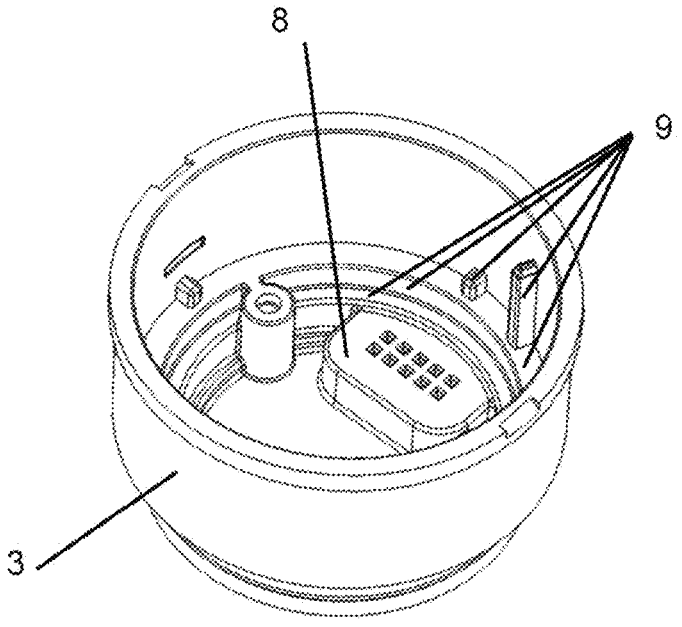
FIG. 5 is a perspective view of the body of a housing cartridge for a sensor for assembly in the measurement equipment of the invention, showing the inside of said body.
Figure 6:
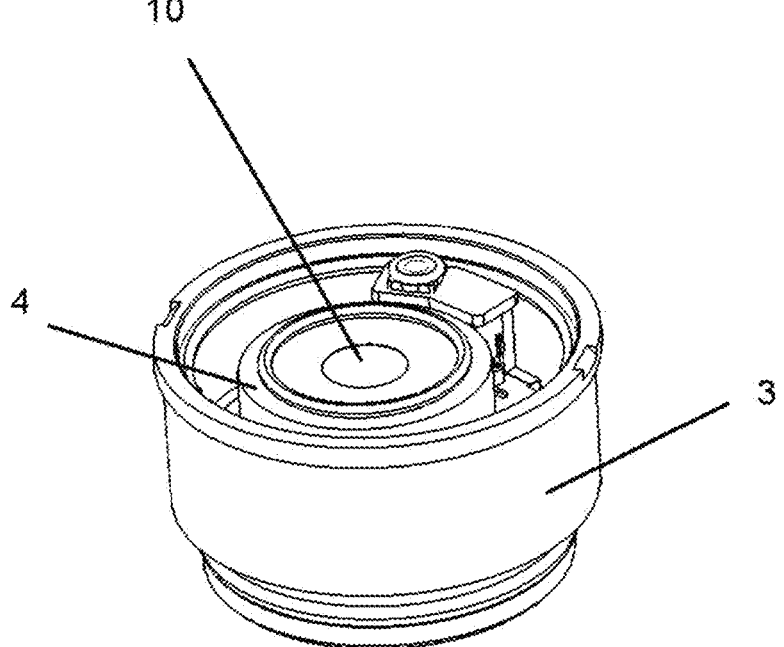
FIG. 6 is a perspective view of the body of a cartridge housing therein a unitary assembly of a sensor and its specific electronic board.
Figure 7:
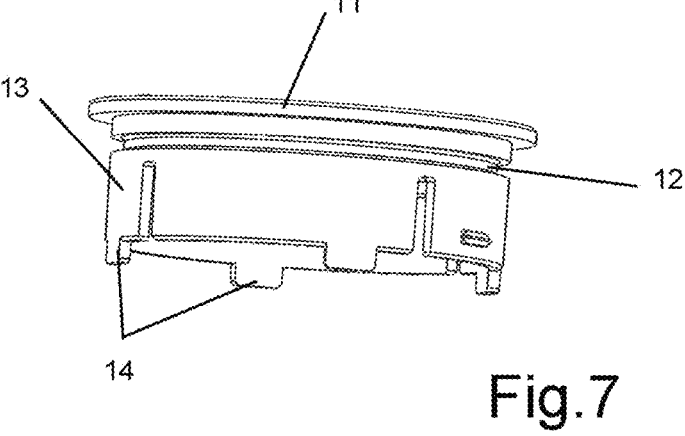
FIG. 7 is a side perspective view of a closing lid of a cartridge of the equipment object of the invention.
Figure 8:
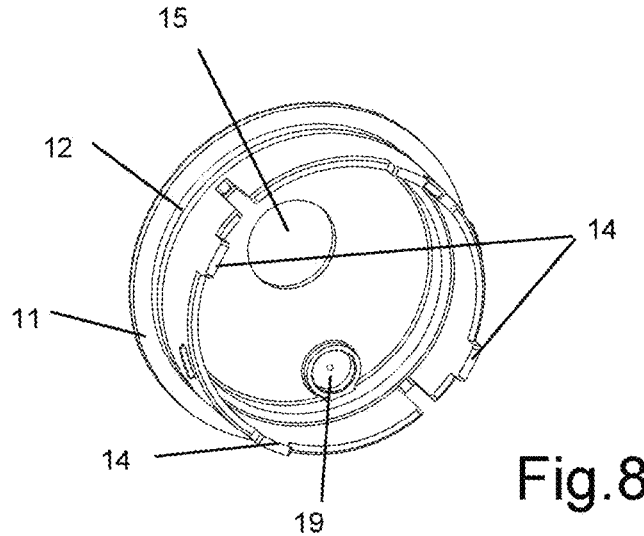
FIG. 8 is a perspective view of the lid of the preceding figure seen from the bottom.
Figure 9:
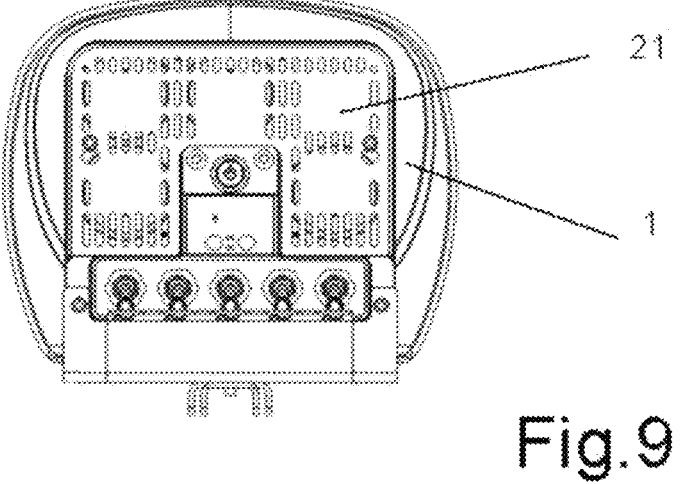
FIG. 9 is a plan view of measurement equipment according to the invention, incorporating a grid above the cartridges housing the measurement sensors.
Figure 10:
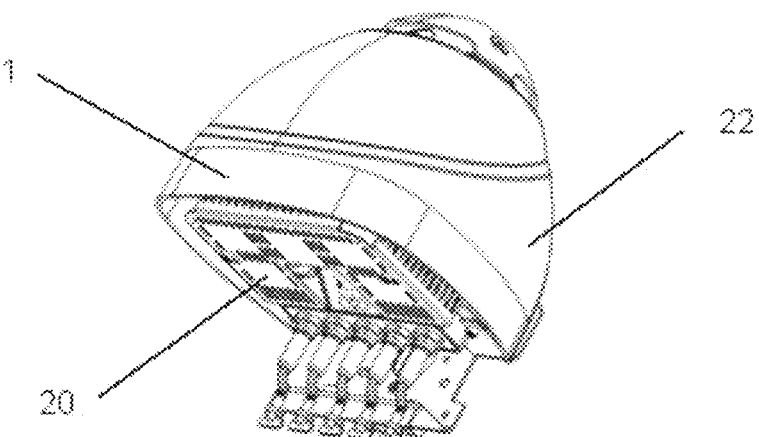
FIG. 10 is a perspective view of measurement equipment according to the invention, incorporating a protective cover over the entire assembly making up the equipment.

In addition, the cartridges (3) have therein a configuration formed by structures (9), preferably in the form of protuberances and/or steps, as can be seen in FIG. 5. Said structures, on which the units formed by the sensors (4) with their specific electronic boards (5) are supported, are located at different heights so that, in each case, the corresponding sensor (4) has an end measurement surface (10) arranged at a set level. In this way, the end surface (10) is always in direct contact with the air. The end measurement surfaces (10) of the sensors (4) of all the cartridges (3) of the measurement equipment must correspond at said level so that the measurements of the environmental parameters performed are correct.

Any type of sensor (4) can therefore be incorporated in each cartridge (3) of the measurement equipment, regardless of its height and shape, providing versatility to the cartridge (3) for the different sensor standards existing on the market. By means of being supported on the corresponding structures (9) inside the cartridge (3), each sensor (4) can be placed with its end measurement surface (10) at the suitable height, whereby the cartridge (3) and accordingly the measurement equipment is universal in terms of the sensors (4) with which they can be equipped.

Each cartridge (3) is closed at the end with a lid (11), which is fitted to the mouth of the cartridge (3) with an O-ring (12) that ensures a hermetic closure. Preferably, the lid (11) furthermore has a skirt (13), even more preferably it is provided with protrusions (14) on its edge, whereby it presses on the specific electronic board (5) of the sensor (4) that is housed inside the cartridge (3), thereby ensuring the positioning in the assembly inside the cartridge (3) and the electrical connection of the unitary assembly of the sensor (4) with its specific electronic board (5) in the assembly inside the cartridge (3).

Said lid (11) of the cartridges (3) has an opening (15) with which the end measurement surface (10) of the sensors (4) coincides in their assembly position inside the cartridges (3), such that said end measurement surfaces (10) of the sensors (4) are in contact with the outside air through said opening (15) of the lids (11) to measure the environmental parameters that have to be controlled. According to one embodiment, said opening (15) is arranged off-centered such that it allows the end surface (10) of the different types of sensors (4) to coincide, including those with a rectangular arrangement. It is also provided that said opening (15) is preferably configured to be able to couple at said point the nozzle of a machine or calibration tool that uses a control gas. In this way, by means of a recess (not shown), the fitting thereof is therefore allowed, introducing a specific gas to observe the reaction of the sensor.

To ensure leak-tightness, in addition to the O-ring (12), it is alternatively provided to arrange a gasket between the end surface (10) of the sensor and the lid (11), such that external elements are prevented from entering the inside of the cartridge through the hole (15). Additionally, the cartridge (3) comprises a gasket that is arranged between the hole (2) of the housing (1) and the outer surface of the cartridge (3), which prevents external elements from entering the equipment through the connector (7).

Preferably, the lid (11) comprises in the skirt (13) at least one groove in correspondence with a protrusion of the inner wall of the cartridge (3), such that rotation and misalignment of the opening (15) with respect to the sensor (4) are prevented.

However, it is envisaged to place blind lids (11) in the cartridges (3) that are empty only for the purpose of covering a hole (2) in the housing (1) where no sensor (4) has to be incorporated and the housing (1) is thereby hermetically sealed.

Given that some factors, such as temperature, humidity, atmospheric pressure and others, can affect the measurements made by the sensors (4), distorting the values of said measurements, there can be arranged connected to the central electronic board probes (16) for measuring said factors so that the appropriate corrections on the measurement values provided by the sensors (4) can be made.

For this to be effective, the measurement of the influencing factors must be performed at the same level/height as the end measurement surfaces (10) of the sensors (4), so the mentioned probes (16) are arranged such that their end is located at said level of the end measurement surfaces (10) of the sensors (4) of the cartridges (3), for which there are envisaged in the housing (1) battlements (17) where said probes (16) are installed in the event that it is necessary to complement the measurement.

For the same purpose, complementary mini sensors for measuring temperature and humidity, which must in turn be arranged at the same level as the end measurement surfaces (10) of the sensors (4), can be incorporated in the actual specific electronic boards (5) of the sensors (4) by means of connectors (18), so there is provided in the lids (11) of the cartridges (3) a blind hole (19) which can be broken, when required, so that the mini sensors connected to the specific electronic board (5) of the sensor (4) housed inside the corresponding cartridge (3) can come into contact with the outside air through said blind hole.

The measurement equipment is completed with an electronic communications board (20), with which the central electronic board (6) is connected, such that information is transmitted remotely to maintain traceability of the quality of the measurement and its final validity/expiration date. In this way, the status and information of each sensor is indicated on a display to anticipate its replacement and in the event that it expires, the measurements are invalidated.

It is envisaged to incorporate in the equipment a grid (21), covering the cartridges (3), preferably made of stainless steel with a specific pattern of cavities and solid parts, which prevents sunlight or strong air currents from directly striking the end measurement surfaces (10) of the sensors (4), the measurement functions of which may be impaired by these factors.

Similarly, in order to prevent the detrimental impact of sunlight or strong air currents, it is envisaged to incorporate a protective cover (22) over the assembly of the measurement equipment, said cover being provided with openings for allowing the passage of circulating air that comes into contact with the sensors (4), so that the air quality evaluation measurements that the equipment must perform can be carried out. Preferably, the protective cover (22) comprises a canopy in the upper above a gap which results in air inlet openings. This is useful to ensure that the sensors are, at most, always at the same room temperature, regardless of whether there is too much or too little solar radiation. This also is useful so that, in the presence of strong winds, the air flows more quickly between the cover (22) and the housing (1), cooling the equipment more quickly.

The invention claimed is:

1. A measurement equipment for measuring gases and environmental parameters, the measurement equipment comprising:
   a housing comprising a first body comprising a plurality of holes, each hole adapted to hold a removable cartridge, and a central electronics board disposed within the first body;
   a plurality of removable cartridges holding a plurality of sensors adapted to detect respective parameters, each removable cartridge adapted to fit interchangeably into any one of the plurality of holes of the housing, each removable cartridge comprising:
   a second body comprising an internal cavity and a mouth;
   a lid adapted to fit onto the mouth of the second body, the lid comprising an opening;
   a cartridge electronics board disposed within the internal cavity of the removable cartridge; and
   a sensor attached to the cartridge electronics board; and
   a plurality of connectors disposed in the housing, each connector adapted to connect a respective cartridge electronics board of a respective cartridge to the central electronics board;

wherein the internal cavity of each of the plurality of removable cartridges comprises a plurality of step structures located at different vertical positions within the internal cavity, wherein each of the plurality of step structures has a different respective horizontal surface and a different respective width corresponding to different vertical positions, wherein each of the plurality of step structures is adapted to support a respective cartridge electronics board and a respective sensor having to the corresponding width at respective the corresponding vertical position within the internal cavity of the respective removable cartridge, wherein each of the plurality of step structures in each removable cartridge is adapted to allow a respective sensor to be held within the respective removable cartridge in a corresponding vertical position selected to ensure that an end measurement surface of the respective sensor is at a same height as other end measurement surfaces of other sensors in other removable cartridges held in the plurality of holes of the housing.

2. The measurement equipment for measuring gases and environmental parameters according to claim 1, wherein the plurality of connectors are coupled to the central electronic board.

3. The measurement equipment for measuring gases and environmental parameters according to claim 1, further comprising temperature and humidity measurement probes having respective ends at a same height level as respective end measurement surfaces of the plurality of sensors of the plurality of removable cartridges.

4. The measurement equipment for measuring gases and environmental parameters according to claim 1, further comprising a grid arranged above the plurality of removable cartridges, the grid adapted to prevent sunlight and air currents from striking respective end measurement surfaces of the plurality of sensors.

5. The measurement equipment for measuring gases and environmental parameters according to claim 1, further comprising a protective cover covering the measurement equipment, the protective cover having a plurality of side openings adapted to allow a passage of air.

6. The measurement equipment for measuring gases and environmental parameters according to claim 1, wherein each removable cartridge further comprises one or more second sensors adapted to measure temperature and humidity, the one or more second sensors connected to the respective cartridge electronics board of the respective removable cartridge through a second connector arranged at a same height as an end measurement surface of the respective sensor within the respective removable cartridge.

* * * * *